United States Patent [19]

Delhez et al.

[11] Patent Number: 6,072,096
[45] Date of Patent: *Jun. 6, 2000

[54] PROCESS FOR THE PREPARATION OF A CATALYST AND ITS USE FOR THE CONVERSION OF CHLOROALKANES INTO ALKENES CONTAINING LESS CHLORINE

[75] Inventors: Patrice Delhez, Herve; Benoît Heinrichs, Liege; Jean-Paul Pirard, Chenee; Jean-Paul Schoebrechts, Grez-Doiceau, all of Belgium

[73] Assignee: Solvay (Societe Anonyme), Brussels, Belgium

[ * ] Notice: This patent issued on a continued prosecution application filed under 37 CFR 1.53(d), and is subject to the twenty year patent term provisions of 35 U.S.C. 154(a)(2).

[21] Appl. No.: 08/645,330

[22] Filed: May 13, 1996

[30] Foreign Application Priority Data

May 24, 1995 [BE] Belgium ................................ 09500468

[51] Int. Cl.⁷ ...................................................... C07C 1/26
[52] U.S. Cl. ........................... 585/641; 585/638; 502/325; 502/330; 502/331; 502/333; 502/344; 502/347
[58] Field of Search ..................................... 502/158, 333, 502/325, 330, 331, 344, 347; 585/641, 638; 208/262.1; 526/281

[56] References Cited

U.S. PATENT DOCUMENTS 4,547,600 10/1985 Cosyns et al. .
5,346,681 9/1994 Pachaly et al. .
5,453,557 9/1995 Harley et al. ........................... 585/641

FOREIGN PATENT DOCUMENTS

| 0177198 | 6/1985 | European Pat. Off. . |
| 0177198 | 4/1986 | European Pat. Off. . |
| 0583783 | 2/1994 | European Pat. Off. . |
| 0629442 | 12/1994 | European Pat. Off. . |
| 2536410 | 5/1984 | France . |
| 01159054 | 6/1989 | Japan . |
| 93/06926 | 9/1993 | WIPO . |
| 94/07827 | 4/1994 | WIPO . |

OTHER PUBLICATIONS

J. Phillips et al.: "Phase Behavior of Palladium–Silver Particles Supported on Silica". In: J. Phys. Chemc., 1993, vol. 97, No. 14, pp. 3565–3570.

*Primary Examiner*—Thomas Dunn
*Attorney, Agent, or Firm*—Venable

[57] ABSTRACT

Process for the preparation of a catalyst including a metal of group VIII and a metal of group Ib, according to which the mixture including the alkoxide precursor of an inorganic oxide and complexes including the metals of group VIII and Ib and difunctional complexing compounds including an electron-donor group and a hydrolysable group is hydrolysed in order to form a gel. Process for the conversion of chloroalkanes into alkenes containing less chlorine by means of hydrogen, using such a catalyst.

18 Claims, No Drawings

PROCESS FOR THE PREPARATION OF A CATALYST AND ITS USE FOR THE CONVERSION OF CHLOROALKANES INTO ALKENES CONTAINING LESS CHLORINE

FIELD OF THE INVENTION

The invention relates to a process for the preparation of a catalyst including a metal of group VIII and a metal of group Ib on a support including an inorganic oxide, and to a process for conversion of chloroalkanes into alkenes containing less chlorine by means of hydrogen in the presence of this catalyst.

TECHNOLOGY REVIEW

In International Application WO-94/07827 a process is described for conversion of chloroalkanes into alkenes containing less chlorine by means of hydrogen in the presence of a bimetallic catalyst including a metal of group VIII and a metal of group Ib on a support. In this known process it is preferred to employ a support made of active carbon. Catalysts including a metal of group VIII and a metal of group Ib on an inorganic oxide support are known in the state of the art. In a known process for the synthesis of a catalyst including palladium and silver on silica the silica support is first of all impregnated with a solution including palladium, is dried, the support including the palladium is subjected to a calcination and a reduction and then the procedure is repeated with a solution including silver (J. Phys. Chem., 1993, vol. 97, pages 3565 to 3570, J. Phillips et al.). This known process is, however, difficult to carry out. Furthermore, the use of the catalysts thus prepared does not give good results in processes for the conversion of chloroalkanes into alkenes containing less chlorine.

SUMMARY OF THE INVENTION

A process for the preparation of a catalyst including a metal of group VIII and a metal of group Ib on a support including an inorganic oxide has now been found which is simpler, which does not exhibit the disadvantages described above and which gives the catalyst improved properties making it possible in particular to convert chloroalkanes into alkenes containing less chlorine in a good yield and with good selectivity.

DETAILED DESCRIPTION OF THE INVENTION

The invention consequently relates to a process for the preparation of a catalyst including a metal of group VIII and a metal of group Ib on a support including an inorganic oxide, which is characterized in that:

in a first stage a mixture is dissolved in an organic solvent, including an alkoxide precursor of the inorganic oxide, a complex of a compound of the metal of group VIII and of a difunctional complexing compound corresponding to the general formula

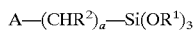
$$A-(CHR^2)_a-Si(OR^1)_3$$

in which
  a is an integer from 0 to 8,
  $R^1$ is an alkyl chain containing from 1 to 8 carbon atoms,
  $R^2$ is a hydrogen atom or an alkyl chain containing from 1 to 4 carbon atoms,
  A denotes an electron-donor group capable of complexing the metal of group VIII, and a complex of a compound of the metal of group Ib and of a difunctional complexing compound corresponding to the general formula

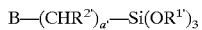
$$B-(CHR^{2'})_{a'}-Si(OR^{1'})_3$$

in which
  a' is an integer from 0 to 8,
  $R^{1'}$ is an alkyl chain containing from 1 to 8 carbon atoms,
  $R^{2'}$ is a hydrogen atom or an alkyl chain containing from 1 to 4 carbon atoms,
  B denotes an electron-donor group capable of complexing the metal of group Ib;

in a second stage the mixture is hydrolysed in order to form a gel; and in a third stage the gel is dried.

A difunctional complexing compound is intended to denote a compound containing at least two functional groups, the first group being a hydrolysable group of the formula $-Si(OR^1)_3$, or respectively $-Si(OR^{1'})_3$ in which $R^1$, or respectively $R^{1'}$, denotes an alkyl chain containing from 1 to 8 carbon atoms, the second group being the electron-donor group A, or respectively B. Group A is an electron-donor group capable of complexing the metal of group VIII. Group B is an electron-donor group capable of complexing the metal of group Ib. The electron-donor group may, in particular, be chosen as a function of the metal of group VIII, or respectively of the metal of group Ib, which is used.

The electron-donor group A is advantageously selected from those of general formula

$$R^6R^5N-(CHR^4)_b-N(R^7)-$$

in which $R^4$, $R^5$, $R^6$ and $R^7$ are, independently, selected from a hydrogen atom or an alkyl chain containing from 1 to 4 carbon atoms, and b is an integer from 1 to 4.

The electron-donor group B is advantageously selected from those of general formula

$$R^{6'}R^{5'}N-(CHR^{4'})_{b'}-N(R^{7'})-$$

in which $R^{4'}$, $R^{5'}$, $R^{6'}$ and $R^{7'}$ are, independently, selected from a hydrogen atom or an alkyl chain containing from 1 to 4 carbon atoms, and b' is an integer from 1 to 4, and those of general formula

$$N(R^{3'})_2-$$

in which $R^{3'}$ is a hydrogen atom and/or an alkyl chain containing from 1 to 4 carbon atoms.

In the process according to the invention the metal of group VIII is preferably selected from palladium, platinum, iridium, nickel, cobalt and rhodium. Palladium is particularly preferred.

In an advantageous embodiment of the process according to the invention the metal of group VIII is palladium and the difunctional completing compound which corresponds to it is selected from those of general formula

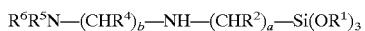
$$R^6R^5N-(CHR^4)_b-NH-(CHR^2)_a-Si(OR^1)_3$$

in which a is an integer from 1 to 4, b is an integer from 1 to 3, $R^1$ is an alkyl chain containing from 1 to 4 carbon atoms, $R^2$, $R^4$, $R^5$ and $R^6$ are, independently, selected from a hydrogen atom and a methyl or ethyl chain. Very particularly preferred are the compounds corresponding to the general formula

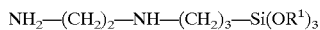
$$NH_2\text{—}(CH_2)_2\text{—}NH\text{—}(CH_2)_3\text{—}Si(OR^1)_3$$

in which $R^1$ is an alkyl chain containing from 1 to 4 carbon atoms. In this embodiment of the process the palladium compound is preferably an organic palladium compound. Palladium acetylacetonate is particularly preferred.

In the process according to the invention the metal of group Ib is preferably selected from copper and silver. Silver is particularly preferred.

In an advantageous embodiment of the process according to the invention the metal of group Ib is silver and the difunctional complexing compound which corresponds to it is selected from those of the general formula

$$R^{6'}R^{5'}N\text{—}(CHR^{4'})_{b'}\text{—}NH\text{—}(CHR^{2'})_{a'}\text{—}Si(OR^1)_3$$

in which a' is an integer from 1 to 4, b' is an integer from 1 to 3, $R^1$ is an alkyl chain containing from 1 to 4 carbon atoms, $R^{2'}$, $R^{4'}$, $R^{5'}$ and $R^{6'}$ are, independently, selected from a hydrogen atom and a methyl or ethyl chain, and those of general formula

$$N(R^{3'})_2\text{—}(CHR^{2'})_{a'}Si(OR^1)_3$$

in which a' is an integer ranging from 1 to 4, $R^1$ is an alkyl chain containing from 1 to 4 carbon atoms, $R^{2'}$ and $R^{3'}$ are, independently, selected from a hydrogen atom and a methyl or ethyl chain. Very particularly preferred are the compounds corresponding to the general formula

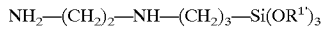
$$NH_2\text{—}(CH_2)_2\text{—}NH\text{—}(CH_2)_3\text{—}Si(OR^{1'})_3$$

or to the general formula

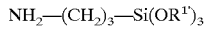
$$NH_2\text{—}(CH_2)_3\text{—}Si(OR^{1'})_3$$

in which $R^{1'}$ is an alkyl chain containing from 1 to 4 carbon atoms. In this embodiment of the process the silver compound is preferably an organic silver compound. Silver acetate is particularly preferred.

In the process according to the invention, the alkoxide precursor of the inorganic oxide is preferably selected from silicon, aluminium, titanium and zirconium alkoxides. According to an alternative form of the process according to the invention a mixture of alkoxides may be used. Good results have been obtained with silicon alkoxides corresponding to the general formula $Si(OR^8)_4$ in which $R^8$ is an alkyl chain containing from 1 to 6 carbon atoms.

In the process according to the invention the function of the organic solvent is to dissolve the alkoxide precursor of the inorganic oxide, the complex of a compound of the metal of group VIII and the complex of a compound of the metal of group Ib in order to form a homogeneous solution. The organic solvent is preferably selected from alcohols. Particularly preferred are the lower alcohols containing fewer than 5 carbon atoms.

In the first stage of the process according to the invention a mixture including the alkoxide precursor of the inorganic oxide, the complex of a compound of the metal of the group VIII and the complex of a compound of the metal of group Ib is dissolved in the organic solvent. The order in which these three compounds are introduced into the organic solvent is not critical, nor are the respective quantities, provided that a homogeneous solution is obtained. The relative quantities of the complexes and of the alkoxide precursor used will determine the relative quantities of the metal of group VIII and of the metal of group Ib on the support including the inorganic oxide. The quantities which are used may vary within wide limits. The quantities of the complexes and of the alkoxide precursor are usually adjusted to obtain a catalyst containing at least 0.05% by weight of the metal of group VIII. These quantities are preferably adjusted so as to obtain a catalyst containing at least 0.5% by weight of the metal of group VIII. They are usually adjusted so as to obtain a catalyst in which the quantity of metal of group VIII does not exceed 15% by weight. These quantities are preferably adjusted so as to obtain a catalyst in which the quantity of metal of group VIII does not exceed 10% by weight. In a particularly preferred manner the quantities used are chosen in order to obtain a catalyst containing 5% or less of metal of group VIII. These quantities are usually adjusted to obtain a catalyst containing at least 0.05% by weight of the metal of group Ib. These quantities are preferably adjusted so as to obtain a catalyst containing at least 0.5% by weight of the metal of group Ib. These quantities are usually adjusted so as to obtain a catalyst in which the quantity of metal of group Ib does not exceed 15% by weight. These quantities are preferably adjusted so as to obtain a catalyst in which the quantity of metal of group Ib does not exceed 10% by weight. In a particularly preferred manner the quantities used are chosen in order to obtain a catalyst containing 5% or less of metal of group Ib.

The relative quantities of the complex of a compound of the metal of group VIII and of the complex of a compound of the metal of group Ib will determine the weight ratio of the metal of group VIII to the metal of group Ib in the catalyst. The relative quantities of these two complexes are preferably adjusted so as to obtain a catalyst in which the weight ratio of the metal of group VIII to the metal of group Ib is at least 0.1. In a particularly preferred manner these quantities are adjusted in order to obtain a weight ratio of at least 0.4. They are preferably adjusted so as to obtain a catalyst in which the weight ratio of the metal of group VIII to the metal of group Ib does not exceed 10. In a particularly preferred manner these quantities are adjusted in order to obtain a weight ratio which does not exceed 2.5.

In the second stage of the process according to the invention the mixture obtained in the first stage is hydrolysed with water so as to obtain a gel. The quantity of water which is used in this second stage must be at least sufficient to hydrolyse the alkoxide precursor and the hydrolysable groups of formula —$Si(OR^1)_3$, or respectively —$Si(OR^{1'})_3$ of the difunctional complexing compounds of the complexes of the compounds of the metals of group VIII and Ib respectively. A slight excess of water is preferably used. The hydrolysis water used in the second stage of the process is usually at a pH equal to or higher than 7. This pH may be, for example, obtained by using the hydrolysis water in the state of an ammoniacal aqueous solution. The hydrolysis is advantageously performed by adding the hydrolysis water slowly and with stirring to the mixture prepared in the first stage of the process. The water may optionally be diluted with an organic solvent, preferably the same organic solvent as that used in the first stage of the process. After the addition of water to the mixture originating from the first stage the reaction mixture is advantageously stored in a closed receptacle, preferably at a temperature higher than 50° C., for a period which is at least sufficient to form a gel, usually a period varying from a few hours to a few days.

In the third stage of the process according to the invention the gel obtained in the second stage of the process is dried. The function of the drying is to remove the solvent from the gel.

According to a first alternative form of embodiment of the third stage of the process the gel is dried in supercritical conditions. Super-critical conditions are intended to denote conditions in which the temperature and the pressure are above the critical temperature and the critical pressure of the liquid present in the gel. This liquid essentially includes the organic solvent used, the excess water and the residual products of hydrolysis. Drying the gel in supercritical conditions makes it possible to obtain a catalyst including the support in the form of an aerogel.

According to another alternative form of embodiment of the third stage of the process, which is preferred, the gel is dried at a pressure which is lower than atmospheric pressure. In this alternative form of the process the drying pressure and temperature may vary within broad limits. The drying temperature is preferably higher than or equal to 50° C. Good results have been obtained by drying the gel at a temperature of between 60° C. and 200° C., at a pressure of approximately 10 mbar for several days. Drying the gel in these conditions makes it possible to obtain a catalyst containing the support in the form of a xerogel.

The process according to the invention for the preparation of a catalyst may advantageously include a fourth stage, which consists in calcination the dried gel originating from the third stage of the process. The calcination is intended to remove the organic residues from the gel. The calcination may advantageously be performed in a stream of oxygen or of air, at a temperature which is higher than or equal to 200° C. and does not exceed 800° C.

The process according to the invention for the preparation of a catalyst may advantageously also include a subsequent stage of treatment in a reducing atmosphere, in order to obtain the metals of group VIII and IB in the elementary state in the catalyst. This reduction usually consists in treating the dried gel under a reducing atmosphere, such as, for example, hydrogen, at a temperature of at least 100° C. and preferably lower than or equal to 500° C.

The process according to the invention makes it possible to obtain a homogeneous dispersion of the metals of groups VIII and Ib, in a finely divided state, of dimensions of the order of a few nanometers, in the support including the inorganic oxide. The process of preparation according to the invention makes it possible in particular to obtain the metals of group VIII and Ib in the form of an alloy on the support.

Consequently, the invention also relates to a catalyst including a metal of group VIII and a metal of group Ib on a support including an inorganic oxide capable of being obtained by means of the process for preparation according to the invention, described above.

The catalyst originating from the process for preparation according to the invention may be employed in a large number of industrial processes. It is especially suitable for hydrogenation reactions. The catalyst originating from the process of preparation according to the invention is particularly well-suited for converting chloroalkanes into alkenes containing less chlorine, by means of hydrogen.

Consequently, the invention also relates to a process for converting chloroalkanes into alkenes containing less chlorine, by means of hydrogen, which is characterized in that a catalyst capable of being obtained by means of the process for preparation according to the invention, described above, is used.

The chloroalkanes used in the process according to the invention are alkanes containing at least 1 chlorine atom. Acyclic chloroalkanes are preferred. Acyclic chloroalkanes of general formula $C_nH_{2n+2-x}Cl_x$ in which n=2 to 6 and x=1 to (2n+2) are especially advantageous. Particularly preferred are chloroethanes and chloropropanes and more especially dichloroethanes, dichloropropanes and trichloropropanes. 1,2-Dichloroethane and 1,2-dichloropropane are very particularly preferred.

Alkenes containing less chlorine are intended to denote the alkenes in which the number of carbon atoms corresponds to the number of carbon atoms in the chloroalkane used and which have at least one chlorine atom fewer than the chloroalkane used. The alkene containing less chlorine as defined in the present invention may therefore contain no chlorine atom. In the case of chloroalkanes of general formula $C_nH_{2n+2-x}Cl_x$ in which x=1 to (2n+2) the alkenes formed therefore correspond to the general formula $C_nH_{2n-y}Cl_y$ in which y may vary from 0 to (x−1).

In the process according to the invention the function of the hydrogen is to convert the chloroalkane into an alkene containing less chlorine, as set out above. The hydrogen may optionally be mixed with another gas which is inert in the conditions of the reaction of conversion of the chloroalkane into alkene containing less chlorine. The other gas employed may be a gas from the group of the inert gases properly so called, such as helium, or a gas which does not take part in the above-mentioned reaction, such as an alkene. The quantity of hydrogen per unit volume is preferably at least 5% of the total volume of hydrogen and of the other gas.

The hydrogen/chloroalkane molar ratio is preferably at least 0.1, more particularly at least 0.5. This ratio preferably does not exceed 40. In a particularly preferred manner it does not exceed 20.

The process according to the invention may be performed in liquid phase or in gaseous phase. The process according to the invention is preferably performed in gaseous phase. The process is preferably performed at a temperature of at least 150° C., more particularly of at least 200° C. The temperature usually does not exceed 450° C. It preferably does not exceed 400° C. The pressure at which the process is performed is not critical in itself. The operation is usually carried out at a pressure of at least 1 bar. The pressure generally does not exceed 30 bar. It preferably does not exceed 10 bar.

The catalyst used in the process according to the invention may be any catalyst capable of being obtained by means of the process for preparation according to the invention, described above. A catalyst including palladium and silver is preferably used. The quantity of palladium in the catalyst is advantageously at least 0.05%, preferably at least 0.5%, by weight. The quantity of palladium usually does not exceed 10% by weight. It preferably does not exceed 5%. The quantity of silver on the support is advantageously at least 0.05%, preferably at least 0.5%, by weight. The quantity of silver usually does not exceed 10% by weight. It preferably does not exceed 5%. The weight ratio of palladium to silver is preferably at least 0.1. In a particularly preferred manner this weight ratio is at least 0.4. The palladium/silver weight ratio preferably does not exceed 10. In a particularly preferred manner this ratio does not exceed 2.5. The palladium/silver weight ratio is advantageously selected so as to obtain a palladium/silver alloy on the support. A catalyst including the support in the form of a xerogel is preferably used.

The process according to the invention for conversion of chloroalkanes into alkenes containing less chlorine makes it possible to obtain high conversions of chloroalkanes and high selectivities for the alkenes containing less chlorine which are sought after, without appreciable formation of alkanes or chloroalkanes. The process according to the invention additionally has the advantage that the deactivation of the catalyst in the course of time is particularly slow and that the regeneration of the catalyst can be carried out easily, especially by means of air.

The process according to the invention finds an advantageous application in the conversion of chloropropanes into propylene, and more particularly of chloropropanes formed as by-products in the manufacture of allyl chloride by chlorination of propylene and/or in the manufacture of epichlorohydrin by hypochlorination of allyl chloride. Examples of chloropropane by-products of these manufactures are especially 1,2-dichloropropane and 1,2,3-trichloropropane. This particular application of the process according to the invention is particularly advantageous because it makes it possible to obtain propylene with a high selectivity, enabling it to be recycled to the stage of chlorination of propylene to allyl chloride.

EXAMPLES

The invention is illustrated more fully by the following examples.

Example 1

(preparation of a catalyst, in accordance with the invention)

Three separate solutions were prepared:

Solution No. 1: 1.2 ml of 3-(2-aminoethylamino) propyltrimethoxysilane were added, with magnetic stirring, to a solution containing 0.8417 g of palladium acetylacetonate and 45.5 ml of ethanol until a clear solution was obtained;

Solution No. 2: 2.6 ml of 3-aminopropyltriethoxysilane were added, with magnetic stirring, to a solution including 0.9143 g of silver acetate and 45.5 ml of ethanol until a clear solution was obtained;

Solution No. 3: 91 ml of ethanol were added to 27.8 ml of a 0.18M aqueous $NH_3$ solution.

Solution No. 2 was poured, with stirring, into a reactor containing solution No. 1 and then 66.3 ml of tetraethyl orthosilicate were added. Solution No. 3 including water was added dropwise and with vigorous stirring to the mixture obtained. The reactor was closed hermetically and was placed in an oven heated to 70° C. The formation of a gel was observed after approximately 15 minutes. The gel was stored in the oven.

After 3 days' aging the gel was dried in an oven maintained under vacuum (12 mbar pressure) and heated to 80° C. for 2 days and then at 150° C. for 3 days.

The xerogel obtained was calcined in a calciner under a stream of air at 400° C. for 8 h and then treated with hydrogen at 350° C. for 3 h.

The catalyst obtained was found to contain 1.5% by weight of palladium and 3% by weight of silver. X-ray diffraction and electron microscopy analyses showed that the metals were finely dispersed on the support, the particle size being approximately 3 nm. X-ray diffraction analysis of the catalyst showed that the metals were present in the form of an alloy including 63 atom % of silver and 37 atom % of palladium.

Example 2

(preparation of a catalyst, in accordance with the invention)

The procedure described in Example 1 was repeated by using a solution No. 2 containing only half of the 3-aminopropyltriethoxysilane and of the silver acetate.

The catalyst obtained was found to contain 1.5% by weight of palladium and 1.5% by weight of silver. X-ray diffraction and electron microscopy analyses showed that the metals were finely dispersed on the support, the particle size being approximately 3 nm. X-ray diffraction analysis of the catalyst showed that the metals were present in the form of an alloy including 47 atom % of silver and 53 atom % of palladium.

Example 3

(preparation of a catalyst in accordance with the invention)

The procedure described in Example 1 was repeated by using a solution No. 2 including only a quarter of the 3-aminopropyltriethoxysilane and of the silver acetate.

The catalyst obtained was found to contain 1.5% by weight of palladium and 0.75% by weight of silver. X-ray diffraction and electron microscopy analyses showed that the metals were finely divided on the support, the particle size being approximately 2.5 nm. X-ray diffraction analysis of the catalyst showed that the metals were present in the form of an alloy including 34 atom % of silver and 66 atom % of palladium.

Example 4

(in accordance with the invention)

The catalyst obtained in Example 2 was employed for converting 1,2-dichloroethane into ethylene. For this purpose 0.11 g of the catalyst of Example 2 were introduced into a tubular reactor. The reactor containing the catalyst was then fed at a rate of 1 Sl/h of 1,2-dichloroethane, 2 Sl/h of hydrogen and 37 Sl/h of helium, at 300° C., at 3 bar. The mean contact time, that is to say the ratio of the volume occupied by the catalyst to the total feed rate was estimated at 0.13 s.

1,2-Dichloroethane conversion was 8% and the selectivity for ethylene (defined as the molar fraction of 1,2-dichloroethane which has reacted and which has been converted into ethylene) was 100%.

Example 5

(reference)

Example 4 was repeated using 0.25 g of a catalyst containing 1.5% by weight of palladium and 1.5% by weight of silver, not in accordance with the invention, prepared by the known impregnation technique described in J. Phys. Chem., 1993, vol. 97, pages 3565 to 3570, J. Phillips et al. For this purpose, in order to prepare the catalyst, a silica support (Graces grade 1352) was impregnated with solutions of $Pd(NH_3)_4(OH)_2$ and of $AgNO_3$.

1,2-Dichloroethane conversion was 14% and the selectivity for ethylene was 85%.

On comparing the results obtained in Examples 4 and 5 respectively, in the same operating conditions and with catalysts containing the same quantity of palladium and silver, it is seen that the catalyst obtained by means of the process according to the invention (Example 4) is markedly more selective for ethylene than the catalyst prepared according to the technique of the prior art (Example 5).

Example 6

(in accordance with the invention)

The catalyst obtained in Example 2 was employed for converting 1,2-dichloropropane into propylene. For this purpose 0.28 g of the catalyst of Example 2 were introduced into a tubular reactor. The reactor containing the catalyst was then fed at a rate of 0.75 Sl/h of 1,2-dichloropropane, 1.5 Sl/h of hydrogen and 5.25 Sl/h of helium, at 300° C., at 3 bar. The residence time was determined as 1.7 s.

1,2-Dichloropropane conversion was 25% and the selectivity for propylene was 89%.

What is claimed is:

1. A process for the preparation of a catalyst including a metal of group VIII and a metal of group Ib on a support including an inorganic oxide, in which:

in a first stage a mixture is dissolved in an organic solvent, including an alkoxide precursor of the inorganic oxide, a complex of a compound of the metal of group VIII and of a difunctional complexing compound corresponding to the general formula

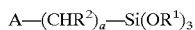

in which a is an integer from 0 to 8, $R^1$ is an alkyl chain containing from 1 to 8 carbon atoms, $R^2$ is a hydrogen atom or an alkyl chain containing from 1 to 4 carbon atoms, A denotes an electron-donor group capable of complexing the metal of group VIII, and a complex of a compound of the metal of group Ib and of a difunctional complexing compound corresponding to the general formula

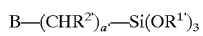

in which a' is an integer from 0 to 8, $R^1$ is an alkyl chain containing from 1 to 8 carbon atoms, $R^{2'}$ is a hydrogen atom or an alkyl chain containing from 1 to 4 carbon atoms, B denotes an electron-donor group capable of complexing the metal of group Ib;

in a second stage the mixture is hydrolysed in order to form a gel; and in a third stage the gel is dried.

2. The process according to claim 1, in which the metal of group VIII is palladium and the metal of group Ib is silver.

3. The process according to claim 1, in which the electron-donor group A is a group selected from those of general formula

in which $R^4$, $R^5$, $R^6$ and $R^7$ are, independently, selected from a hydrogen atom or an alkyl chain containing from 1 to 4 carbon atoms and b is an integer from 1 to 4, and the electron-donor group B is a group selected from those of general formula

in which $R^{4'}$, $R^{5'}$, $R^{6'}$ and $R^{7'}$ are, independently, selected from a hydrogen atom or an alkyl chain containing from 1 to 4 carbon atoms, and b' is an integer from 1 to 4, and those of general formula

in which $R^{3'}$ is a hydrogen atom or an alkyl chain containing from 1 to 4 carbon atoms.

4. The process according to claim 1, in which the metal of group VIII is palladium and the compound completing this metal corresponds to the general formula

in which a is an integer from 1 to 4, b is an integer from 1 to 3, $R^1$ is an alkyl chain containing from 1 to 4 carbon atoms, $R^2$, $R^4$, $R^5$ and $R^6$ are, independently, chosen from a hydrogen atom and a methyl or ethyl chain.

5. The process according to claim 1, in which the compound of the metal of group VIII is palladium acetylacetonate and the compound completing this metal corresponds to the general formula $$NH_2-(CH_2)_2-N-(CH_2)_3-Si(OR^1)_3.$$

6. The process according to claim 1, in which the metal of group Ib is silver and the compound completing this metal corresponds to the general formula

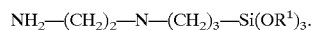

or to the general formula

in which a' is an integer from 1 to 4, b' is an integer from 1 to 3, $R^1$ is an alkyl chain containing from 1 to 4 carbon atoms, $R^{2'}$, $R^{3'}$, $R^{4'}$, $R^{5'}$ and $R^{6'}$ are, independently, selected from a hydrogen atom and a methyl or ethyl chain.

7. The process according to claim 1, in which the compound of the metal of group Ib is silver acetate and the compound completing this metal corresponds to the general formula

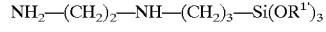

or to the general formula $$NH_2-(CH_2)_3-Si(OR^{1'})_3.$$

8. The process according to claim 1, in which the alkoxide precursor of the inorganic oxide is selected from silicon, aluminium, titanium and zirconium alkoxides.

9. The process according to claim 1, in which the respective quantities of the complexes and of the alkoxide precursor are adjusted so as to obtain a catalyst containing from 0.05% to 15% by weight of the metal of group VIII and from 0.05% to 15% by weight of the metal of group Ib.

10. The process according to claim 1, in which the respective quantities of the complexes are adjusted so as to obtain a catalyst in which the weight ratio of the metal of group VIII to the metal of group Ib is from 0.1 to 10.

11. The process according to claim 1, in which in the third stage the gel is dried at a pressure which is lower than atmospheric pressure in order to obtain a xerogel.

12. A catalyst including from 0.05% to 15% by weight of a metal of group VIII selected from palladium, platinum, iridium, nickel, cobalt and rhodium and from 0.05% to 15% by weight of a metal of group Ib selected from copper and silver on a support including an inorganic oxide obtained by means of the process according to claim 1.

13. In a catalyzed process for hydrogenation of chloroalkanes into alkenes containing less chlorine, the improvement comprising a catalyst according to claim 12.

14. The process according to claim 13, in which the chloroalkanes are chosen from chloroethanes and chloropropanes.

15. The catalyst according to claim 12, wherein said metal from group VII is palladium, and said metal of group Ib is silver.

16. The catalyst according to claim 12, wherein said metal of group VIII is palladium present in an amount from 0.5% to 5%.

17. The catalyst according to claim 15, wherein the palladium/silver rate ratio is from 0.4 to 2.5.

18. The catalyst according to claim 15, wherein the palladium/silver are present in the form of an alloy.

* * * * *